United States Patent [19]

Banasiak

[11] 4,262,156
[45] Apr. 14, 1981

[54] OLEFIN DISPROPORTIONATION

[75] Inventor: Dennis S. Banasiak, Bartlesville, Okla.

[73] Assignee: Phillips Petroleum Co., Bartlesville, Okla.

[21] Appl. No.: 118,896

[22] Filed: Feb. 6, 1980

Related U.S. Application Data

[62] Division of Ser. No. 58,985, Jul. 20, 1979, Pat. No. 4,245,738.

[51] Int. Cl.$^3$ .............................................. C07C 6/00
[52] U.S. Cl. ................................... 585/411; 585/643; 585/645; 585/646; 585/647
[58] Field of Search ................ 585/643, 645, 646, 647

[56] References Cited

U.S. PATENT DOCUMENTS

| | | | |
|---|---|---|---|
| 3,637,893 | 1/1972 | Singleton | 585/645 |
| 3,689,433 | 9/1972 | Kroll et al. | 585/645 |
| 4,024,201 | 5/1977 | Takahashi | 585/643 |

OTHER PUBLICATIONS

Chem. Ab. 85:4789s, 1976.
J. Chem. Soc. Chem. Comm., 1202–1203, 1971.

*Primary Examiner*—Veronica O'Keefe

[57] ABSTRACT

A process and a catalyst for the disproportionation of olefins is disclosed wherein the catalyst consists essentially of (1) at least one neutral tungsten carbene complex, (2) at least one halogenated promoter, and (3) at least one tin promoter.

23 Claims, No Drawings

OLEFIN DISPROPORTIONATION

This application is a divisional of copending application Ser. No. 58,985, filed July 20, 1979 now U.S. Pat. No. 4,248,738.

This invention relates to the disproportionation of olefins. More specifically this invention relates to a novel catalyst system and a novel process for the disproportionation of olefins.

The disproportionation or metathesis of olefins is a reaction in which one or more olefinic compounds are transformed into other olefins of different molecular weights. The disproportionation of an olefin to produce one olefin of a higher molecular weight and one olefin of a lower molecular weight can also be referred to as a self-disproportionation. For example, propene can be disproportionated to ethylene and cis- and trans-2-butene. Another type of disproportionation involves the codisproportionation of two different olefins to form still other olefins. For example, the reaction of one molecule of 2-butene with one molecule of 3-hexene can produce two molecules of 2-pentene.

Several catalyst systems have been proposed for the disproportionation of olefins. Several disadvantages have been observed for these catalyst systems. In some cases, isomerization of the double bond of the starting material or product occurs and disproportionation involving the isomeric olefin yields a mixture of products which is difficult to separate. With certain catalysts, polymerization of the olefins occurs at long reaction times or high reaction temperatures. Some catalysts cause alkylation of aromatic solvents with the olefin, thereby consuming some of the reactant or product and producing a more complex product mixture. Some catalysts are only effective for terminal olefins and other catalysts may be effective only with internal olefins. Many of the metathesis catalyst systems use organoaluminum compounds which are expensive and present operational difficulties during production, storage, and use.

An object of the present invention is to provide a novel disproportionation catalyst which produces very little undesirable olefin isomerization and which does not require the employment of expensive organoaluminum components.

Another object of the present invention is to provide a process for the disproportionation of olefins.

Other objects, features and advantages of the present invention will appear more fully from the following description.

SUMMARY OF INVENTION

In accordance with the instant invention, olefins can be disproportionated using a novel homogeneous catalyst consisting essentially of (1) at least one neutral tungsten carbene complex, (2) at least one halogenated promoter, and (3) at least one tin promoter.

THE CATALYST SYSTEM

The carbene complex component of the catalyst system of this invention is a neutral, i.e., non-ionic, carbene complex having the general formula I

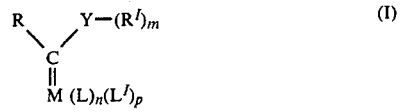

wherein R is an aryl or substituted aryl radical containing from 6 to about 30 carbon atoms per radical and with the aryl substituents being one or more or a mixture selected from a group consisting of halides, alkoxides, and alkyl radicals containing 1 to 20 carbon atoms per radical, $R^I$ is selected from a group consisting of alkyl, cycloalkyl, aryl, substituted aryl, trialkylsilyl, or triarylsilyl radicals containing from 1 to 30 carbon atoms per radical with the aryl substituents being the same as for R described above, Y is O, Se, S, N, or P, m is 1 when Y is O, Se, or S and m is 2 when Y is N or P, M is tungsten or rhenium, each L is a neutral ligand individually selected from the group consisting of CO, NO, $PF_3$, $PCl_3$, and pyridine, $L^I$ is cyclopentadienyl, and p is 0 or 1, and when p is 0, n is 5 and when p is 1, n is 2. Mixtures of ligand L can be used if desired. Specific examples of neutral carbene complexes include (methoxyphenylcarbene)pentacarbonyltungsten(0), (p-chlorophenylmethoxycarbene)pentacarbonyltungsten(0), (p-methylphenylmethoxycarbene)pentacarbonyltungsten(0), (p-methoxyphenylmethoxycarbene)-pentacarbonyltungsten(0), (phenoxyphenylcarbene)-pentacarbonyltungsten(0), (cyclohexyloxyphenylcarbene)pentacarbonyltungsten(0), (butoxyphenylcarbene)pentacarbonyltungsten(0), (octyloxphenylcarbene)pentacarbonyltungsten(0), (hexadecyloxyphenylcarbene)pentacarbonyltungsten(0), (eicosyloxyphenylcarbene)pentacarbonyltungsten(0), (phenyltrimethylsiloxycarbene)pentacarbonyltungsten(0), (phenyltriphenylsiloxycarbene)pentacarbonyltungsten(0), (methylthiophenylcarbene)pentacarbonyltungsten(0), (dimethylaminophenylcarbene)pentacarbonyltungsten(0), (methoxyphenylcarbene)pentanitrosyltungsten(0), and (methoxyphenylcarbene)$\eta^5$-cyclopentadienyl-dicarbonylrhenium(1). Mixtures of carbene complexes can be used if desired.

The presently preferred catalysts are those of formula I wherein R is a phenyl radical, Y is oxygen, $R^I$ is an alkyl radical containing 1 to about 10 carbon atoms per radical, m is 1, L is CO or NO, n is 5, and p is 0.

For reasons of ease of preparation and reactivity, the currently most preferred carbene complex is

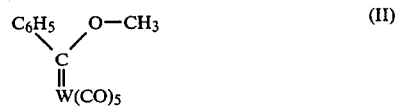

wherein $C_6H_5$ is a phenyl group.

The carbene complexes can be prepared by any of several published procedures, for example: D. J. Cardin, et al, Chem. Rev., 72 545 (1972). D. J. Cardin, et al, Chem. Soc. Rev., 2, 99 (1973). C. P. Casey, in "Transition Metal Organometallic in Organic Synthesis", Vol. 1, H. Alper, Ed., Academic Press, 1976, pp. 189–233. "Inorganic Synthetis" Vol. 17, 95–99 (1979). In a typical preparation, carbene complex II is prepared by reacting tungsten hexacarbonyl with phenyllthium and then with the trimethyloxonium tetrafluoroborate.

The second component of the catalyst system of this invention can be termed a halogenated promoter or activator and is selected from at least one compound selected from the group consisting of fully halogenated methanes and halogenated unsaturated organo compounds having 3 to 30 carbon atoms per molecule, no hydrogens other than those bound to the ring carbons of an aromatic ring, and a fully halogenated alkyl group bonded to the carbon of an olefinic carbon-carbon double bond, a ketone carbonyl double bond, or an aromatic carbon-carbon double bond, and wherein the halogens of the halogenated promoter are individually selected from chlorine, bromine, and iodine.

Examples of suitable halogenated methane activators include carbon tetrachloride, carbon tetrabromide, dibromodichloromethane, bromotrichloromethane, carbon tetraiodide, dichlorodiiodomethane, iodotrichloromethane, and the like. The presently preferred halogenated methane activators are carbon tetrachloride, carbon tetrabromide, and bromotrichloromethane.

Examples of suitable halogenated organo compound unsaturated activators include hexachloroacetone, hexachloropropene, α,α,α-trichlorotoluene, α,α,α-tribromotoluene, p-di(trichloromethyl)benzene, 1,3,5-tri(-trichloromethyl)benzene, hexachlorocyclobutanone, and the like. The presently preferred unsaturated halide activators are hexachloroacetone, hexachloropropene, and α,α,α-trichlorotoluene.

Mixtures of any of the halide activators (including both the halogenated methanes and the unsaturated halides) can be used if desired.

The third component of the catalyst system of this invention can be termed a tin promoter or activator and is either a tetraorganotin or an organotrihalotin compound.

The tetraorganotin activator contains 4 to 40 carbon atoms per molecule and can be represented by the following general formula III:

$$SnR_4^{II} \qquad (III)$$

wherein each $R^{II}$ contains 1 to 10 carbon atoms per radical and is independently selected from a group consisting of alkyl, cycloalkyl, aryl, and substituted aryl radicals wherein the substituents are each independently selected from alkyl or alkoxy radicals or halides such as chloride or bromide.

Examples of suitable tetraorganotin activators include tetramethyltin, tetraethyltin, tetrapropyltin, tetrabutyltin, tetraoctyltin, tetradecyltin, tetracyclopentyltin, tetracyclooctyltin, tetraphenyltin, tetra(p-methylphenyl)tin, tetra(p-methoxyphenyl)tin, tetra(p-chlorophenyl)tin, and the like.

For reasons of availability and reactivity the currently preferred tetraorganotin activators are those in which each $R^{II}$ in formula III is an alkyl radical containing 1 to 4 carbon atoms per radical. Examples of the currently preferred tetraorganotin activators include tetramethyltin, tetraethyltin, and tetrabutyltin.

The organotrihalotin activator contains 1 to 10 carbon atoms per molecule and can be represented by the following general formula IV:

$$R^{II}SnX_3 \qquad (IV)$$

wherein $R^{II}$ is as defined previously and X is chloride, bromide, or iodide.

Examples of suitable organotrihalotin activators include methyltrichlorotin, propyltrichlorotin, propyltriiodotin, butyltrichlorotin, butyltribromotin, butyltriiodotin, octyltrichlorotin, octyltribromotin, decyltrichlorotin, phenyltrichlorotin, p-methylphenyltrichlorotin, p-methoxyphenyltrichlorotin, p-chlorophenyltrichlorotin, and the like.

For reasons of availability and reactivity, the currently preferred organotrihalotin activators are those of general formula IV wherein $R^{II}$ is an alkyl radical containing 1 to 6 carbon atoms per molecule and X is chloride or bromide. Examples of the currently preferred organotrihalotin activators include methyltrichlorotin, propyltrichlorotin, butyltrichlorotin, and butyltribromotin.

Mixtures of two or more of the above described tin activators can be used if desired.

The activators and the carbene complex are combined in any amounts which provide a catalytic effect upon disproportionation of an olefin, i.e., 1-pentene or a mixture of olefins.

The ratio of the catalyst components can be expressed in terms of a mole ratio of activator to carbene complex. Generally, the molar ratio of halogenated activator to carbene complex in the present invention is from about 1/1 to about 1000/1 and preferably is from about 5/1 to about 100/1. And generally the molar ratio of the tin activator to the carbene complex is from about 1/1 to about 1000/1 and preferably is from about 5/1 to about 100/1. In addition, generally the mole ratio of the halogenated activator to the tin activator is from about 1/10 to about 20/1 and is preferably from about 1/1 to about 5/1.

The catalyst of the present invention is employed in a catalytically effective amount. The amount of catalyst employed in the process of this invention can be expressed in terms of the molar ratio of olefin to carbene complex component. Generally, the molar ratio of olefinic reactant to carbene component is from about 1/1 to about 5000/1 and preferably from about 50/1 to about 500/1.

OLEFIN REACTANTS

The process of this invention involves the contacting of two olefinic reactants, which may be the same olefin or different olefins, in the presence of the catalyst system described above. It is considered that the catalyst of this invention is generally suitable for the disproportionation of any of the olefins that are disproportionated by earlier conventional techniques. Typically, at least one of the olefinic reactants contain 3 to 30 carbon atoms per molecule and contains one or more carbon-carbon double bonds.

Generally, at least one of the olefinic reactants contains one or two non-conjugated carbon-carbon double bonds and is either an acyclic olefin represented by the formula V:

$$R^{III}CH=CHR^{IV} \qquad (V)$$

wherein $R^{III}$ and $R^{IV}$ are independently selected from a group consisting of hydrogen, alkyl radicals, and alkenyl radicals with each of the radicals containing 1 to 18 carbon atoms per radical, or a monocyclic olefin represented by the following formula VI:

wherein $R^V$ is an alkylene or alkenylene radical containing 5 to 16 carbon atoms and wherein each of the radicals $R^{III}$, $R^{IV}$, and $R^V$ can contain one or more halides, e.g. chloride, bromide, provided the halides are at least two carbons from the carbon of the olefinic bond, and each of the radicals can contain one or more aryl or alkyl-substituted aryl groups, provided the aryl or alkyl-substituted aryl radicals are at least one carbon from the carbons of the olefinic bond.

For reasons of availability and reactivity, the currently preferred olefinic reactants are those of general formula V wherein $R^{III}$ and $R^{IV}$ are selected from hydrogen and alkyl radicals containing 1 to 10 carbon atoms per radical.

Examples of suitable acyclic olefinic reactants include propene, 1-butene, 1-pentene, 2-pentene, 1-hexene, 2-hexene, 3-hexane, 1-octene, 2-octene, 4-methyl-1-heptene, 1-decene, 2-decene, 1-dodecene, 4-dodecene, 1-tetradecene, 1-hexadecene, 1-eicosene, 1,4-hexadiene, 4-chloro-1-butene, 4-phenyl-1-butene, and 4-phenyl-1-octene.

Examples of suitable monocylic olefins include cycloheptene, cyclooctene, cyclononene, cyclotetradecene, 4-chloro-1-cyclooctene, 1,5-cyclododecadiene, and 1,6-cyclodecadiene.

Examples of the currently preferred olefinic reactants include propene, 1-butene, 1-pentene, 2-pentene, 2-hexene, 1-octene, 1-decene, and the like.

When two different olefinic reactants are utilized in the disproportionation, one of the olefins generally must be an acyclic or monocyclic olefin as described above and the other olefin can be either another acyclic or monocyclic olefin as described above or can be ethylene, a monocyclic monoolefin containing 4 to 6 carbons in the ring, e.g., cyclobutene, cyclopentene, and cyclohexene, or polycyclic mono- or diolefins, i.e., olefins that generally do not undergo self disproportionation. Examples of suitable polycyclic olefins include bicyclo[2.2.2]oct-2-ene, bicyclo[2.2.2]oct-2,5-diene, bicyclo[2.2.1]hept-2-ene, and bicyclo[3.3.0]oct-2-ene.

When two different olefinic reactants are employed in the disproportionation process, the molar ratio of one olefinic reactant to the other olefinic reactant is not critical, and generally up to a 20-fold excess, preferably up to a 2-fold excess of one olefinic reactant can be employed.

REACTION CONDITIONS

The disproportionation reaction of this invention can be carried out under any suitable reaction conditions. Generally the reaction is carried out at temperatures in the range of about 35° C. to about 150° C. While lower temperatures can be used, the reaction rates are generally too low to be of interest. Temperatures above 150° C. can be used, but excess decomposition or halogenation of the reaction components can occur. The preferred reaction temperatures are from about 50° C. to about 100° C.

The pressure during the disproportionation reaction is generally in the range of about atmospheric to about 1500 psig (10341 kiloPascals gauge-kPa). Preferably, the pressure is from about atmospheric to about 500 psig (3447 kPa).

The disproportionation can be carried using a basically inert diluent or diluents such as saturated hydrocarbons, e.g., hexane, octane, cyclohexane, aromatic hydrocarbons, e.g., benzene, toluene, or halogenated compounds, e.g., "chlorobenzene" methylene chloride, bromoform can be used. Many of the halogenated promoters of this invention can serve as the sole diluent at the upper end of the ranges set forth those promoters. The amount of basically inert diluent can be expressed as a volume ratio of diluent to the halogenated promoter portion of the catalyst system. Suitable volume ratios of diluent to halogenated promoter can be from about 0/1 to about 500/1 and preferably from about 1/1 to about 100/1.

The presence of oxygen and water has been found to be deleterious to the disproportionation reaction and should be substantially avoided during the reaction. Inert gases such as nitrogen or helium can be used to maintain a dry, inert atmosphere during the reaction.

The reaction time period depends on the reaction temperature and pressure as well as on the nature of the particular catalyst system and olefinic reactant used. The reaction time is generally from about 30 minutes to several days. Preferably the reaction time is from about 5 to about 120 hours. Generally, internal olefins, such as 2-pentene, disproportionate at a slower rate than terminal olefins, such as 1-pentene, and longer reaction times are required than for terminal olefins.

REACTION PRODUCT WORKUP

The reaction product mixture from the disproportionation can be worked up using any combination of conventional separation and purification techniques. The unreacted starting olefins, the olefin products, the diluent (if used), and the activator can frequently be separated by fractional distillation. The unreacted starting olefin, diluent, and activator can be recycled to the reaction zone if desired. The olefin products can be purified by conventional techniques such as crystallization, distillation, or extractions.

The carbene catalyst can be removed, if desired, by the addition of dilute aqueous ammonia to decompose and precipitate the catalyst, followed by filtration and extraction. The resultant organic layer can then be worked up in a conventional manner.

REACTION PRODUCTS

According to the process of this invention, two olefinic reactants are disproportionated to form a product containing one or two olefins having a total number of carbon atoms equal to the sum of the carbon atoms of the two olefinic reactants and having a number of ethylenic double bonds equal to the sum of the ethylenic double bonds of the reactants.

One variation of the process comprises the disproportionation of two molecules of the same olefinic reactant. The reaction of two molecules of an acyclic olefin of formula V generally produces one olefin of a higher carbon number and one olefin of a lower carbon number as depicted in equation (1)

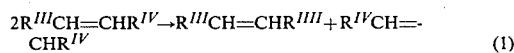
(1)

wherein $R^{III}$ and $R^{IV}$ have the previously stated significance. If $R^{III}$ and $R^{IV}$ represent identical groups, it is appreciated that the disproportionation reaction will not cause any skeletal changes as the products $R^{III}CH=CHR^{III}$ and $R^{IV}CH=CHR^{IV}$ will be equivalent to $R^{IV}CH=CHR^{III}$. By way of specific illustration, the reaction of two molecules of propylene produces ethylene and 2-butene. However, the reaction of two molecules of 2-butene produces two molecules of 2- butene. When $R^{III}$ and $R^{IV}$ of formula V are combined to form a cyclic olefin (VI), the reaction of two molecules of the cyclic olefin produces a single cyclic diolefin. At high dilution the cyclic diolefin can be isolated, but in more concentrated solutions, further disproportionation frequently occurs to form materials of higher molecular weight. By way of specific illustration, the reaction of two molecules of cyclooctene in a dilute reaction mixture produces 1,9-cyclohexadecadiene.

Another variation of the process comprises the disproportionation of two different acyclic olefinic reactants. By way of specific illustration, the reaction of 2-butene and 3-hexene produces two molecules of 2-pentene and the reaction of propene with isobutene produces one molecule of isopentene and molecule of ethylene.

Still another variation of the process is "ring-opening" disproportionation wherein an acyclic olefin reactant (V) is contacted with a cyclic olefinic reactant (VI). The product of "ring-opening" is a single olefinic compound with one less carbocyclic ring than in VI.

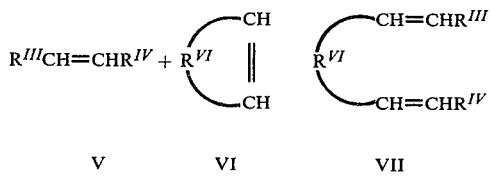

V        VI        VII wherein $R^{III}$ and $R^{IV}$ are as previously defined and $R^{VI}$ is an alkylene or alkylene radical containing 4 to 16 carbon atoms. By way of specific illustration, from reaction of 2-butene and cyclopentene is produced 2,7-nonadiene. Other typical products include 2,8-decadiene produced by reaction of cyclohexane and 2-butene, 3,8-undecadiene produced from 3-hexane and cyclopentene, 1,5,9-decatriene produced by reaction of ethylene and 1,5-cyclooctadiene, and 1,4-divinylcyclohexane from ethylene and bicyclo[2.2.2]oct-2-ene.

PRODUCT UTILITY

The olefinic products, for the most part, have established utility as precursors of polymers, e.g., as the third component of ethylene-propylene terpolymers useful as synthetic elastomers.

The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

EXAMPLES

The olefins used in the following examples were commercial materials which were purified by contact with silica gel and were stored over 4 A molecular sieves before use. All solvents and most liquid halogenated materials were distilled from drying agents appropriate for the material and were stored over 4 A molecular sieves before use. Some of the tin compounds were stored over 4 A molecule sieves before use and some were used as received.

The carbene complexes were prepared by published procedures by reacting the appropriate metal compound with an organolithium compound followed by reaction with trimethyloxonium tetrafluoroborate. For example, tungsten hexacarbonyl was reacted with phenyllithium and was then reacted with trimethyloxonium tetrafluoroborate to form (methoxyphenylcarbene)pentacarbonyltungsten(0), viz.

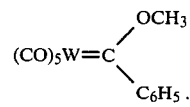

The carbene complexes were stored in a desiccator in a freezer before use in a reaction. Since the carbene complexes sometimes lose activity during prolonged storage, it is currently preferred that the carbene complex be used within about three weeks of preparation.

Each of the runs in the following examples was carried out in a 10 oz. beverage bottle equipped with a magnetic stirrer, a self-sealing elastomeric liner, and a three-hole crown cap. The liquid reaction components were charged to the dried, nitrogen flushed bottle by syringe through the cap. Solids were added to the bottle before attaching the cap. The reaction mixture was heated to the desired temperature and stirred at the reaction temperature for the desired time period. At the conclusion of the reaction time period, the reaction mixture was analyzed by gas-liquid chromatography (glc). The glc peak areas were converted to weights using an internal standard. Since 2 molecules of 1-pentene are disproportionated to 1 molecule of ethylene and 1 molecule of 4-octene, the yields of 4-octene are expressed as a mole percent yield based on one-half of the number of moles of 1-pentene charged to the reactor. The ethylene product was not determined and the 4-octene is a mixture of cis- and trans-isomers. 2-Pentene disproportionates to 2-butene and 3-hexene. In the 2-pentene runs, the 2-butene level was not determined and the yield of 3-hexene is expressed as a mole percent yield based on one-half of the number of moles of 2-pentene charged to the reactor.

EXAMPLE I

Three control runs were carried out in the absence of the halogenated promoter component and the tin promoter component of the catalyst system of the present invention. In run 1, 1.54 g (22 mmoles) of 1-pentene and 4.4 ml of a solution of

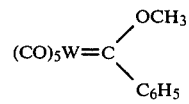

(0.11 mmoles) in chlorobenzene was charged to the reaction bottle. The mixture was stirred at room temperature (about 24° C.) for 24 hours. A glc analysis indicated that no reaction had occurred. The mixture was heated to 130° C. and stirred for 48 hours. Another glc analysis of the reaction mixture showed that no reaction had occurred.

In run 2, 1.54 g (22 mmoles) of 1-pentene, 4.4 ml of a solution

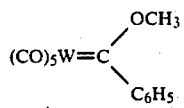

(0.22 mmoles) in hexane, and 10 ml of hexane were charged to the reaction bottle. The reaction mixture was stirred at 55° C. for 4 days. A glc analysis of the reaction mixture showed that no reaction had occurred.

In run 3, 1.54 g (22 mmoles) of 2-pentene, 4.4 ml of a solution of

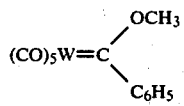

(0.11 mmoles) in hexane and 2 ml of hexane were charged to the reaction bottle. The reaction mixture was stirred at 140° C. for 20 hours. A glc analysis showed that no disproportionation had occurred.

The results of these runs show that neutral carbene complexes in the absence of activators are not effective for the disproportionation of olefins.

EXAMPLE II

This example sets forth runs carried out using 1-pentene as the olefin reactant in disproportionation in the presence of catalyst systems within the scope of the present invention. In each run, the reactor was charged with 1.54 g (22 mmoles) of 1-pentene, 4.4 ml of a hexane solution of

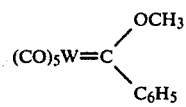

(0.22 mmoles in all runs except run 9 where 0.11 mmoles were used), additional hexane in some runs, and various halide and/or tin compounds. The total amounts of hexane in each run varied from 4.4 ml to about 14.4 ml. The halides and tin compounds and the amounts used as well as the reaction times, temperatures, and results are shown in Table I.

TABLE I

| Run No. | Halide, mmoles | Compound, mmoles | Reaction Conditions Temp., °C. | Time, hrs. | 4-Octene Yield,[a] mole % |
|---|---|---|---|---|---|
| 4 | $CCl_4$, 0.2 | None | 55 | 96 | 0 |
| 5 | $CCl_4$, 3 | None | 55 | 23 | 0 |
| 6 | $CCl_4$, 52 | None | 55 | 24 | 16.4 |
| 7 | None | $SnMe_4$, 22 | 55 | 96 | 0 |
| 8 | None | $SnMe_4$, 2.2 | 55 | 96 | 0 |
| 9 | None | $SnMe_4$, 1.1 | 130 | 48 | 0 |
| 10 | $CCl_4$, 3 | $SnMe_4$, 2.2 | 55 | 22 | 17.2 |
| 11 | $CCl_4$, 52 | $SnMe_4$, 1.1 | 55 | 24 | 14.6 |
| 12 | $CCl_4$, 3 | $SnMe_4$, 2 | 150 | 22 | 7.3 |
| 13 | $CCl_4$, 3 | $SnEt_4$, 2 | 55 | 72 | 26.7 |
| 14 | $Cl_3CCCCl_3$, 3 (O) | None | 55 | 72 | 3.6 |
| 15 | $Cl_3CCCCl_3$, 3 (O) | $SnMe_4$, 2 | 55 | 24 | 10.8 |
| 16 | $Cl_3CCCCl_3$, 3 (O) | $SnMe_4$, 2 | 55 | 120 | 37.7 |
| 17 | $Cl_3C-C(Cl)=CCl_2$, 3 | None | 55 | 72 | 1.7 |
| 18 | $Cl_3C-C(Cl)=CCl_2$, 3 | $SnMe_4$, 2 | 55 | 24 | 7.8 |
| 19 | $Cl_3C-C(Cl)=CCl_2$, 3 | $SnMe_4$, 2 | 55 | 120 | 25.8 |
| 20 | $Cl_3C-C(Cl)=CCl_2$, 3.3 | $BuSnCl_3$, 3 | 55 | 20 | 4 |
| 21 | $\phi CCl_3$[b], 3 | None | 55 | 20 | t |
| 22 | $\phi CCl_3$[b], 3 | $SnMe_4$, 2 | 55 | 72 | 37.2 |
| 23 | $BrCCl_3$, 3 | None | 55 | 20 | 13.2 |
| 24 | $BrCCl_3$, 3 | $SnMe_4$, 2 | 55 | 24 | 17.7 |
| 25 | $CBr_4$, 3 | None | 55 | 68 | t |
| 26 | $CBr_4$, 3 | $SnMe_4$, 2 | 55 | 68 | 5.4 |
| 27 | None | $BuSnCl_3$, 2.2 | 55 | 20 | 0 |
| 28 | $CCl_4$, 3 | $BuSnCl_3$, 2.2 | 55 | 20 | 8.6 |
| 29 | $CCl_4$, 3 | $SnBu_4$, 3 | 55 | 72 | 18.6 |
| 30 | $CCl_4$, 3 | $SnBu_4$, 3 | 80 | 72 | 29.3 |

[a] t = trace
[b] α,α,α-trichlorotoluene

Runs 7 through 9 are control runs which show that tetramethyltin ($SnMe_4$) by itself is not an activator for the carbene complex for olefin disproportionation and runs 4 through 6 show that carbon tetrachloride ($CCl_4$) by itself is an activator for the carbene complex only at the highest level (mole ratio of $CCl_4$/carbene complex of about 235/1 in run 6). Runs 10 through 13 show that the combination of CCl$_4$ and a tetraalkyltin with the carbene complex catalyzes the disproportionation of 1-pentene. The yield in run 11 is slightly below the yield obtained with the same level of CCl$_4$ (run 6) without a tin compound. It is believed that this is a result of a dilution effect of the high CCl$_4$/SnMe$_4$ mole ratio (50/1). Run 12 was carried out at 150° C. and a chlorinated octene was present in the product. Run 12 thus indicates that higher reaction temperatures can result in some chlorination side reactions.

Runs 15, 16, 18, 19, 20, and 22 illustrate the use of a halide containing various types of unsaturation (carbonyl, carbon-carbon olefinic, and aromatic) with a tin compound and a carbene complex to catalyze olefin disproportionation. Control runs 14, 17, and 21 show that the halides without the tin compound are less effective with the carbene complex for disproportionation.

The use of other halides and other tin compounds (butyltrichlorotin-BuSnCl$_3$ and tetrabutyltin-SnBu$_4$) as catalyst system components for olefin disproportionation are illustrated in runs 24, 26, 28, 29, and 30. Runs 23, 25, and 27 show that the individual halides or tin compound with a carbene complex are less effective for olefin disproportionation than the combination of halides and tin compounds with carbene complexes.

The results of the runs in this example demonstrate the use of the catalyst system of the present invention for the disproportionation of olefins.

EXAMPLE III

This example sets forth runs carried out with 2-pentene which demonstrate internal olefin disproportionation using a catalyst system of the present invention. In each run the reactor was charged with 1.54 g. (22 mmoles) of 2-pentene, a chlorobenzene solution of

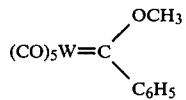

(0.22 mmoles), additional quantities of chlorobenzene, CCl$_4$, and tetramethyltin. The various quantities, reaction conditions, and results are shown in Table II.

TABLE II

| Run No. | CCl$_4$, mmoles | SnMe$_4$ mmoles | Chlorobenzene In Carbene Solution, ml | Total, ml | Reaction Conditions Temp., °C. | Time, hrs. | 3-Hexene Yield, mole % |
|---|---|---|---|---|---|---|---|
| 31 | 1 | 1 | 4.4 | 10 | 55 | 24 | (c) |
| 32 | 3 | 2 | 2.2 | 5.2 | 150 | 22 | 37.8 |
| 33 | 3 | 2 | 4.4 | 14.4 | 55 | 72 | 36.5 |

(c) 3-Hexene was present at a level below about 5 mole percent. Analysis problems prevented a quantitative determination.

The results in Table II demonstrate the process of this invention for the disproportionation of 2-pentene to 3-hexene and 2-butene. Run 31, which used low levels of the carbon tetrachloride and tetramethyltin resulted in a low yield of 3-hexene under the reaction conditions. Internal olefins are known in the art to frequently be more difficult to disproportionate than terminal olefins. It is believed that longer reaction times would have given increased yields of disproportionation products.

EXAMPLE IV

The example presents a series of control runs carried out with several halogen compounds which do not fall within the definition of suitable halides according to the present invention. The runs demonstrate that the halogen compounds are either not effective or are not synergistic with carbene complexes and tin compounds as a catalyst system for olefin disproportionation. In each run, the reactor was charged with 1.54 g (22 mmoles) of 1-pentene, a hexane solution of

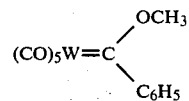

(0.22 mmoles), additional hexane in some runs, a halide, and, in most runs, tetramethyltin. The levels of the various components, the reaction conditions, and the results of the reactions are shown in Table III. Each run was carried out at 55° C.

TABLE III

| Run No. | Halide, mmoles | Tin Compound, mmoles | Reaction Time, hrs. | Hexane In Carbene Solution, ml | Total, ml | 4-Octene Yield mole % |
|---|---|---|---|---|---|---|
| 34 | Cl$_3$CCH$_3$, 3 | None | 20 | 4.4 | 9.4 | 0 |
| 35 | Cl$_3$CCH$_3$, 3 | SnMe$_4$, 2 | 20 | 4.4 | 9.4 | 0 |
| 36 | φCH$_2$Cl, 3 | SnMe$_4$, 2 | 22 | 7.2 | 7.2 | 0 |
| 37 | (CH$_3$)$_3$CCl, 3 | SnMe$_4$, 2 | 22 | 4.4 | 4.4 | 0 |
| 38 | CH$_2$Cl$_2$, 3 | SnMe$_4$, 2 | 20 | 4.4 | 7.4 | 0 |
| 39 | CHCl$_3$, 62 | None | 20 | 4.4 | 9.4 | 0 |
| 40 | CHCl$_3$, 2.5 | SnMe$_4$, 2 | 22 | 8.2 | 8.2 | 0 |
| 41 | CHBr$_3$, 22 | None | 48 | 4.4 | 7.4 | 0 |
| 42 | CHBr$_3$, 3 | SnMe$_4$, 2 | 48 | 4.4 | 7.4 | 0 |
| 43 | CH$_2$Br$_2$, 22 | None | 48 | 4.4 | 7.4 | 0 |
| 44 | CH$_2$Br$_2$, 3 | SnMe$_4$, 2 | 48 | 4.4 | 7.4 | 0 |
| 45 | CH$_3$I, 3 | SnMe$_4$, 2 | 22 | 8.2 | 8.2 | 0 |
| 46 | CH$_3$CH$_2$I, 3 | SnMe$_4$, 2 | 22 | 4.4 | 7.4 | 0 |
| 47 | Cl$_3$CCCl$_3$, 3 | None | 72 | 4.4 | 14.4 | 48.1 |
| 48 | Cl$_3$CCCl$_3$, 3 | SnMe$_4$, 2 | 72 | 4.4 | 14.4 | 46 |

The results in Table III show that halides containing aliphatic hydrogens (runs 34 to 46) are ineffective with tin compounds and carbene complexes for olefin disproportionation. Runs 47 and 48 show that halogenated ethanes lacking the unsaturation as described in the present invention are not synergistic with tin compounds and carbene complexes for olefin disproportionation.

EXAMPLE V

Several control runs were carried out with various compounds in place of the tin compounds as defined in the present invention. In each run, the reaction vessel was charged with 1.54 g (22 mmoles) of 1-pentene, 4.4 ml of a hexane solution of

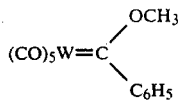

(0.22 mmoles), 0.3 ml (3 mmoles) of CCl$_4$, compound evaluated, and an additional quantity of hexane. Each run was carried out at 55° C. The various compounds, component levels, reaction times, and results are shown in Table IV.

TABLE IV

| Run No. | Total Hexane, ml | Other Compound, mmoles | Reaction Time, hrs. | 4-Octene Yield,[a] mole % |
|---|---|---|---|---|
| 49 | 7.4 | ClSnMe$_3$, 1.3 | 20 | 0 |
| 50 | 9.4 | Sn$_2$Me$_6$, 3 | 20 | t |
| 51 | 9.4 | (SnBu$_3$)$_2$, 2 | 20 | t |
| 52 | 7.4 | Sn(Allyl)$_4$, 2 | (b) | 0 |
| 53 | 9.4 | SiMe$_4$, 2.2 | 20 | 0 |
| 54 | 9.4 | GeMe$_4$, 2 | 20 | 0 |

[a] t = trace
[b] 2 days at 55° C. and 11 days at 25° C.

The results of these runs show that several tin compounds outside the definition of suitable tin compounds in the present invention are ineffective with CCl$_4$ and a carbene complex for catalyzing olefin disproportionation. Tetramethylsilane and tetramethylgermane are also ineffective with CCl$_4$ and a carbene complex for catalyzing olefin disproportionation.

EXAMPLE VI

Another series of control runs was carried out using either metal carbonyl or other carbene complexes in place of the carbene complexes as defined in the present invention. In each run, the reaction bottle was charged with 1.54 g (22 mmoles) of 1-pentene, a metal carbonyl or a hexane solution of a carbene complex, 0.3 ml (3 mmoles) of CCl$_4$, 0.3 ml (2 mmoles) tetramethyltin, and in most runs additional hexane. The metal component, reaction conditions, and reaction results are shown in Table V.

TABLE V

| Run[a] No. | Total Hexane ml | Metal Compound | mmoles | Reaction Time, hrs | 4-Octene Yield,[b] mole % |
|---|---|---|---|---|---|
| 55 | 10 | W(CO)$_6$ | 0.22 | 48 | 0 |
| 56 | 4.4 | 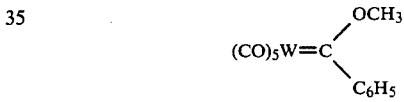 | 0.2 | 20 | t |
| 57 | 9.4 | (CO)$_5$Cr=C(OCH$_3$)(C$_6$H$_5$) | 0.22 | 48 | 0 |
| 58 | 10.8 | (CO)$_5$W=C(OCH$_3$)(CH$_3$) | 0.22 | 72 | 0 |

TABLE V-continued

| Run[a] No. | Total Hexane ml | Metal Compound | mmoles | Reaction Time, hrs | 4-Octene Yield,[b] mole % |
|---|---|---|---|---|---|
| 59 | 16 | (CO)$_4$—W=C(OCH$_3$)(C$_6$H$_5$), P(C$_6$H$_5$)$_3$ | 0.22 | 95 | 0 |

[a] Each run was at 55° C. except run 55, which was at 130° C.
[b] t = trace.

The results in Table V show that tungsten hexacarbonyl [W(CO)$_6$], a molybdenum carbene complex, and a chrominum carbene complex when combined with CCl$_4$ and tetramethyltin are ineffective for the catalysis of the disproportionation of olefins. The data also shows that tungsten carbene complexes containing alkyl groups attached to the carbene carbon or triphenylphosphine ligands attached to the tungsten are not effective disproportionation catalyst system components.

EXAMPLE VII

Two more runs were carried out employing a catalyst system of the present invention in an attempt to obtain self-disproportionation of first cyclopentene and second styrene.

In run 60, the reactor was charged with 1.54 g (22 mmoles) of cyclopentene, 4.4 ml of a hexane solution of

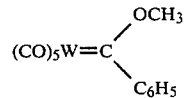

(0.22 mmoles), 0.3 ml (3 mmoles) of CCl$_4$, 0.3 ml (2 mmoles) of tetramethyltin, and 3 ml of hexane. The reaction mixture was stirred at 55° C. for 22 hours. A glc analysis of the reaction product showed that cyclopentene was still present and that no significant amount of self-disproportionation had occurred.

In run 61, the reaction bottle was charged with 2.28 g (22 mmoles) of styrene, 4.4 ml of a hexane solution of (CO)$_5$W=C(OCH$_3$)(C$_6$H$_5$)

(0.22 mmoles), 0.3 ml (3 mmoles) of CCl$_4$, 0.3 ml (2 mmoles) of tetramethyltin, and 5 ml of hexane. The reaction mixture was stirred at 55° C. for 20 hours. A glc analysis showed that only a trace of trans-stilbene was present. cis-Stilbene was not present.

The results of these runs indicate that there are some olefins not particularly suitable for self-disproportionation with the catalyst system of this invention.

While particular embodiments of the present invention have been given for the purpose of illustrating the present invention, those specific examples should not be viewed as limiting the scope of the appended claims.

What is claimed is:

1. A process for the disproportionation of olefins comprising contacting two non-conjugated olefin reactants under disproportionation conditions with a catalytic amount of a catalyst composition consisting essentially of
(1) at least one neutral carbene complex having the general formula

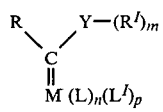

wherein R is an aryl or substituted aryl radical containing 6 to 30 carbon atoms per radical wherein the substituted aryl radical can have one or more substituents each of which can be the same or different and selected from the group consisting of halides, alkoxides and alkyl radicals containing 1 to 20 carbon atoms per radical; $R^I$ is selected from the group consisting of alkyl, cycloalkyl, aryl, substituted aryl, trialkylsilyl, and triarylsilyl radicals containing 1 to 30 carbon atoms per radical with the aryl substituents being the same as for the substituted aryl of R; Y is O, Se, S, N, or P; m is 1 when Y is O, Se, or S and 2 when Y is N or P; M is tungsten or rhenium; each L is individually selected from CO, NO, $PF_3$, $PCl_3$, or pyridine; $L^I$ is cyclopentadienyl; p is 0 or 1; and n is 5 when p is 0 or 2 when p is 1,
(2) at least one halogenated promoter selected from the group consisting of fully halogenated methanes and halogenated unsaturated organo compounds having 3 to 30 carbon atoms per molecule, no hydrogens other than those bonded to the ring carbons of an aromatic ring, and a fully halogenated alkyl radical bonded to the carbon of an olefinic carbon-carbon double bond, a ketone carbonyl double bond, or an aromatic carbon-carbon double bond and wherein the halogens of the halogenated promoters are individually selected from chlorine, bromine, and iodine, and
(3) at least one tin promoter selected from (a) tetraorganotin compounds having 4 to 40 carbon atoms per molecule and the formula

wherein each $R^{II}$ contains 1 to 10 carbon atoms per radical and is individually selected from the group consisting of alkyl, cycloalkyl, aryl, and substituted aryl radicals wherein the substituents are individually selected from alkyl or alkoxy radicals or chloride or bromide, and
(b) organotrihalotin compounds having 1 to 10 carbon atoms per molecule and the formula

wherein $R^{II}$ is as defined above and wherein each X is individually selected from the group consisting of chloride, bromide, and iodide,
wherein said neutral carbene complex of said halogenated promoter, and said tin promoter are present in such amounts as to have a catalytic effect upon the disproportionation of 1-pentene.

2. A process according to claim 1 wherein said disproportionation conditions comprise a temperature in the range of about 35° C. to about 150° C. and a pressure in the range of about atmospheric to about 1,500 psig.

3. A process according to claim 2 wherein said non-conjugated olefinic reactants contain 3 to 30 carbon atoms per molecule and at least one of the olefinic reactants contains a mixture of two olefinic double bonds and is either (1) an acyclic olefin of the formula

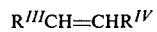

wherein $R^{III}$ and $R^{IV}$ are independently selected from hydrogen, alkyl radicals, alkenyl radicals, or alkyl or alkenyl radicals containing chloride, bromide, aryl, or alkyl-aryl substituents wherein said radicals contain 1 to 18 carbon atoms, the halides are at least two carbon atoms from the carbons of any olefinic bond, and the aryl or alkyl-aryl substituents are at least one carbon from the carbon of any olefinic bond or (2) a monocyclic olefin of the formula

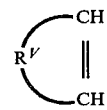

wherein $R^V$ is an alkylene or alkylene radical, or an alkylene or alkylene radical containing chloride, bromide, aryl, or alkyl-aryl substituents wherein the halides are at least two carbon atoms from the carbons of any olefinic bond and the aryl or alkyl-aryl substituents are at least one carbon atom from the carbons of any olefinic bond and wherein $R^V$ contains 5 to 16 carbon atoms.

4. A process according to claim 3 wherein the $R^{III}$, $R^{IV}$, and $R^V$ radicals contain only carbon and hydrogen and 1 to 10 carbon atoms per radical.

5. A process according to claim 4 wherein the olefinic reactants consist essentially of olefins of the formula

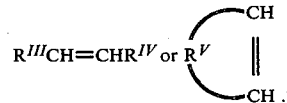

6. A process according to claim 5 wherein the olefnic reactants are selected from the group consisting of 1-butene, 1-pentene, 2-pentene, 1-hexene, 2-hexene, 3-hexene, 1-octene, 2-octene, 4-methyl-1-heptene, 1-decene, 2-decene, 4-dodecene, 1-dodecene, 1-tetradecene, 1-hexadecene, 1-eicosene, 1,4-hexadiene, 4-chloro-1-butene, 4-phenyl-1-butene, and 4-phenyl-1-octene.

7. A process according to claim 6 wherein the molar ratio of said halogenated promoter to said carbene complex is in the range of about 1/1 to about 1000/1, the molar ratio of said tin promoter to said carbene complex is in the range of about 1/1 to about 1000/1, and the molar ratio of the halogenated promoter to the tin promoter is about 1/10 to about 20/1.

8. A process according to claim 7 wherein R is a phenyl radical, Y is oxygen, $R^I$ is a hydrocarbyl alkyl radical containing 1 to 10 carbon atoms, M is tungsten, m is 1, L is CO or NO, n is 5, and p is 0.

9. A process according to claim 8 wherein each said halogenated promoter is selected from at least one compound of the group consisting of fully halogenated methanes, fully halogenated olefins, fully halogenated ketones, and substituted aryl radicals having at least one fully halogenated alkyl substituent.

10. A process according to claim 9 wherein each said tin promoter is selected from at least one compound of the group consisting of said tetraorganotin compounds wherein each $R^{II}$ is an alkyl radical having 1 to 4 carbon atoms and said organotrihalotin compounds wherein each $R^{II}$ is an alkyl radical having 1 to 6 carbon atoms and each X is chloride or bromide.

11. A process according to claim 10 wherein each said halogenated promoter is selected from the group consisting of carbon tetrachloride, carbon tetrabromide, bromotrichloromethane, hexachloroacetone, hexachloropropene, and $\alpha,\alpha,\alpha$-trichlorotoluene, and wherein each said tin promoter is selected from the groups consisting of tetramethyltin, tetraethyltin, tetrabutyltin, methyltrichlorotin, propyltrichlorotin, butyltrichlorotin, and butyltribromotin.

12. A process according to claim 11 wherein L is CO and $R^I$ is a methyl radical in said carbene complex.

13. A process according to claim 12 wherein the molar ratio of said halogenated promoter to said carbene complex is in the range of about 5/1 to about 100/1, the molar ratio of said tin promoter to said carbene complex is in the range of about 5/1 to about 100/1, and the molar ratio of said halogenated promoter to said tin promoter is in the range of about 1/1 to about 5/1.

14. A process according to claim 13 wherein said tin promoter is selected from the group consisting of tetramethyltin, butyltrichlorotin, tetrabutyltin, and tetraethyltin.

15. A process according to claim 14 wherein said olefinic reactants are the same and are of the formula $R^{III}CH=CHR^{IV}$.

16. A process according to claim 15 wherein said disproportionation conditions include a temperature in the range of about 50° C. to about 100° C.

17. A process according to claim 16 wherein said halogenated promoter is carbon tetrachloride.

18. A process according to claim 16 wherein said halogenated promoter is hexachloroacetone.

19. A process according to claim 16 wherein said halogenated promoter is hexachloropropene.

20. A process according to claim 16 wherein said halogenated promoter is $\alpha,\alpha,\alpha$-trichlorotoluene.

21. A process according to claim 16 wherein said halogenated promoter is bromotrichloromethane.

22. A process according to claim 21 wherein said halogenated promoter is tetrabromomethane.

23. A process according to claim 16 wherein said olefinic reactants are 1-pentene.

* * * * *

UNITED STATES PATENT AND TRADEMARK OFFICE
CERTIFICATE OF CORRECTION

PATENT NO. : 4,262,156
DATED : April 14, 1981
INVENTOR(S) : Dennis S. Banasiak

It is certified that error appears in the above-identified patent and that said Letters Patent are hereby corrected as shown below:

Column 15, line 45, delete "$SnR_4^{II}$" and insert therefor --- $SnR_4^{II}$ ---.

Column 16, line 4, delete "mixture" and insert therefor --- maximum ---.

Column 16, line 25, delete "alkylene" second occurrence and insert therefor -- alkenylene --.

Column 16, line 26, delete "alkylene" second occurrence and insert therefor -- alkenylene --.

Signed and Sealed this

Fourteenth Day of July 1981

[SEAL]

Attest:

*Attesting Officer*

GERALD J. MOSSINGHOFF

*Commissioner of Patents and Trademarks*